United States Patent [19]

Stahl et al.

[11] Patent Number: 4,801,536
[45] Date of Patent: Jan. 31, 1989

[54] METHOD FOR PRODUCING HETEROLOGOUS PROTEINS

[75] Inventors: Mark L. Stahl, Arlington; Edward R. LaVallie, Melrose, both of Mass.

[73] Assignee: Genetics Institute, Inc., Cambridge, Mass.

[21] Appl. No.: 57,881

[22] Filed: Jun. 2, 1987

Related U.S. Application Data

[63] Continuation-in-part of Ser. No. 786,749, Oct. 11, 1985, abandoned.

[30] Foreign Application Priority Data

Oct. 10, 1986 [WO] PCT Int'l Appl. .................. PCT/US86/02168

[51] Int. Cl.$^4$ ........................ C12P 21/00; C12N 15/00
[52] U.S. Cl. ................................ 435/68; 435/172.3; 435/320; 935/9; 935/12; 935/29; 935/48
[58] Field of Search .................. 435/68, 172.3; 935/48

[56] References Cited

U.S. PATENT DOCUMENTS 4,338,397  7/1982  Gilbert et al. ........................ 435/68

FOREIGN PATENT DOCUMENTS 0237045  9/1987  European Pat. Off. .

OTHER PUBLICATIONS

Anagnostopoulos & Spizizen, 1961, J. Bacteriol. 81:741–746.
Birnboim & Doly, 1979, Nucleic Acids Res. 7:1513–1523.
Silverman et al., Ann. Rev. Microbiol. 31:397–419, 1977.
Silverman et al., Nature 261:248–250, 1976.
Milhausen et al., Proc. Natl. Acad. Sci. (U.S.A.) 79:6847–6851, 1982.
Bolivar et al., 1977, Gene 2:95–113.
Burnette, 1981, Anal. Biochem. 112:195–203.
Crea & Horn, 1980, Nucleic Acids Res. 8:2331–2348.
Dagert & Ehrlich, 1979, Gene 6:23–28.
Delange et al., 1976, J. Biol. Chem. 254:705–711.
Ferrari et al., 1983, J. Bacteriol. 154:1513–1515.
Fraser & Bruce, 1978, Proc. Natl. Acad. Sci. U.S.A. 75:5836–5940.
Gill & Agabian, 1982, J. Bacteriol. 150:925–933.
Gill & Agabian, 1983, J. Biol. Chem. 258:7395–7401.
Grant & Simon, 1969, J. Bacteriol. 99:116–124.
Grunstein & Hogness, 1975, Proc. Natl. Acad. Sci. U.S.A. 72:3961–3965.
Gryczan et al., 1978, J. Bacteriol. 134:318–329.
Gutterson & Koshland, 1983, Proc. Natl. Acad. Sci. U.S.A. 80:4894–4898.
Hoch, 1976, Adv. Genet. 18:69–98.

(List continued on next page.)

Primary Examiner—Thomas G. Wiseman
Assistant Examiner—Thomas D. Mays
Attorney, Agent, or Firm—David L. Berstein; Bruce M. Eisen

[57] ABSTRACT

This invention concerns a method for producing a heterologous protein in a bacterial host cell such that the protein is exported from the host cell into the culture medium. The method involves culturing in a bacterial culture medium a genetically engineered bacterial strain containing a fusion DNA sequence comprising a first nucleotide sequence encoding at least an N-terminal portion of a flagellin protein and a second nucleotide sequence encoding the heterologous protein. The first nucleotide sequence is linked via its 3' terminus to the 5' terminus of the second nucleotide sequence, and the fusion DNA sequence is itself linked to an expression control sequence. In certain embodiments the first and second nucleotide sequences are linked by means of a linking nucleotide sequence encoding a selectively cleavable polypeptide, In those embodiments the resulting exported fusion protein will contain a selectively cleavable site at which the fusion protein may be selectively cleaved by chemical or enzymatic methods to produce the heterologous protein encoded for by the second nucleotide sequence of the fusion DNA sequence. The heterologous protein may then be separately recovered from any polypeptide fragment of flagellin or other proteinaceous material.

9 Claims, 1 Drawing Sheet

OTHER PUBLICATIONS

Hung & Wensick, 1984, Nucleic Acids Res. 12:1863–1874.
Lino, 1977, Ann. Rev. Genet. 11:161–182.
Joys & Roukis, 1972, J. Biol. Chem. 247:5180–5193.
Kawamura & Doi, 1984, J. Bacteriol. 160:442–444.
Komeda, 1982, J. Bacteriol. 150:16–26.
Laemmli, 1970, Nature 227:680–685.
Lawn et al., 1981, Nucleic Acids Res. 9:6103–6114.
Maniatis et al., 1978, Cell 15:687–701.
Marmur, 1961, J. Mol. Biol. 3:208–218.
Maroux et al., 1971, J. Biol. Chem. 246:5031–5039.
Marston et al., 1984, Biotechnology 2:800–804.
Martinez, 1963, J. Gen. Microbiol. 33:115–120.
Michel & Millet, 1970, J. Appl. Bacteriol. 33:220–227.
Millet, 1970, J. Appl. Bacteriol. 33:207–219.
Nagai & Thogersen, 1984, Nature 309:810–812.
Nilsson et al., 1985, Nucleic Acids Res. 13:1151–1162.
Palva et al., 1983, Gene 22:229–235.
Perlman & Halvorson, 1983, J. Mol. Biol. 167:391–409.
Pooley & Karamata, 1984, J. Bacteriol. 160:1123–1129.
Randall & Hardy, 1984, Microbiol. Rev. 48:290–298.
Richardson, 1971, Proc. Nucleic Acid Res. 2:815–828.
Rigby et al., 1977, J. Mol. Biol. 113:237–251.
Sanger et al., 1977, Proc. Natl. Acad. Sci. U.S.A. 74:5463–5467.
Scherer & Davis, 1979, Proc. Natl. Acad. Sci. U.S.A. 76:4951–4955.
Schoner et al., 1985, Biotechnology 3:151–154.
Shortle, Haber & Botstein, 1982, Science. 217:371–373.
Silhavy et al., 1983, Microbiol. Rev. 47:313–344.
Southern, 1975, J. Mol. Biol. 98:503–517.
Spizizen, 1958, Proc. Natl. Acad. Sci. U.S.A. 44:1072–1078.
Stahl & Ferrari, 1984, J. Bacteriol. 158:411–418.
Suzuki & Komeda, 1981, J. Bacteriol. 145:1036–1041.
Talmadge et al., 1981, Nature. 294:176–178.
Vieira & Messing, 1982, Gene. 19:259–268.
Wahl et al., 1979, Proc. Natl. Acad. Sci. U.S.A. 76:3683–3687.
Watson, 1984, Nucleic Acids Res. 12:5145–5164.
Wickner, 1979, Annu. Rev. Biochem. 48:23–45.
Williams et al., 1982, Science 215:687–688.
Yang et al., 1984, J. Bacteriol. 160:15–21.
Yanisch-Perron et al., 1985, Gene 33:103–119.
Zeig & Simon, 1980, Proc. Natl. Acad. Sci. U.S.A. 77:4196–4200.

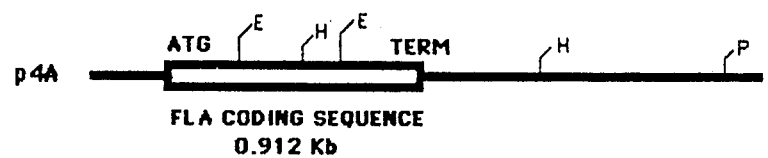
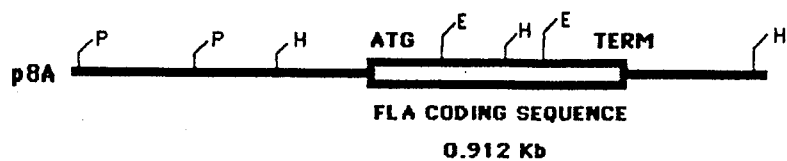

METHOD FOR PRODUCING HETEROLOGOUS PROTEINS

FIELD OF THE INVENTION

This application is a continuation-in-part of U.S. Ser. No. 786,749, filed Oct. 11, 1985, now abandoned.

This invention relates to a novel method for producing a heterologous protein in a bacterial host cell such that the protein is exported from the host cell into the extracellular medium.

Throughout this application various publications are referenced. Full citations for these publications may be found at the end of the specification. The disclosure of these publications are hereby incorporated by reference in order to more fully describe the state of the art to which this invention pertains.

BACKGROUND OF THE INVENTION

Advances in cellular and molecular biology have made it possible, in certain cases, to identify a gene encoding a desired protein, to isolate the gene, to insert the gene into a host cell and to express the inserted gene in the host cell to produce the desired protein. Bacteria, especially *Escherichia coli* and *Bacillus subtilis*, have been intensively studied as host cells. When bacteria are used as host cells for this heterologous gene expression, however, two problems frequently have been encountered. Most bacterial expression systems produce proteins intracellularly. When high level expression is achieved, the protein is often found to be insoluble (Marston et al., 1984; Williams et al.; 1982; Schoner et al., 1985). Production of an active protein from this insoluble material requires solubilization and refolding protocols which are often prohibitively expensive. If the protein is produced in an active, soluble form within the cell, its isolation requires cell lysis which releases hundreds of other soluble intracellular proteins. This can present a formidable problem in purification of the desired product.

Both the problem of production of insoluble, inactive proteins and of difficulty of purification may be overcome by having the bacteria secrete the desired protein into the growth medium. One particularly well documented method of directing the secretion of proteins is the use of a secretory signal sequence (Randall and Hardy, 1984; Silhavy et al., 1983; Wickner, 1979). When a signal peptide is fused to the amino-terminal end of a heterologous protein, it directs the heterologous protein to the secretory machinery at the cell membrane. The heterologous protein is then translocated across the membrane and a specific protease, sometimes referred to as "signal peptidase," removes the signal peptide and releases the heterologous protein. In *E. coli*, secretion results in the accumulation of the heterologous protein in the periplasmic space, while in a gram positive bacterium, such as *B. subtilis*, secretion results in the accumulation of the product in the culture medium. This method has been used to direct the secretion of heterologous proteins in bacteria (Fraser and Bruce, 1978; Palva et al., 1983; Talmadge et al., 1981). As a result of these and other studies, problems, both potential and realized, have been discovered in the use of this particular approach. Cleavage of the signal peptide by signal peptidase may not be efficient or even accurate. Consequently, the secreted population of heterologous protein may contain unprocessed or misprocessed subpopulations. In addition, the amount of heterologous protein secreted is usually very small, and because both *E. coli* and *B. subtilis* also secrete proteases, a significant amount of the heterologous protein can be degraded after it is secreted.

Because of this latter point, the secretion and accumulation of heterologous proteins in the culture medium by *B. subtilis* is vitiated unless the host cell expression and secretion of proteolytic enzymes is minimized or eliminated. One method for minimizing the effect of protease degradation of secreted proteins is to utilize mutant strains deficient in protease production. Mutations have been isolated in both the alkaline and neutral protease structural genes by recombinant methods (Stahl and Ferrari, 1984; Yang et al., 1984; Kawamura and Doi, 1984). Other protease deficient mutations isolated, to date, are pleitropic and also block the formation of mature endospores (Michel and Millet, 1970). Many of these mutations cause the cells to lyse when the culture is in the stationary phase of growth, thus may not be desirable for use in *B. subtilis* for the expression and secretion of heterologous proteins. While the use of existing protease deficient mutants may reduce the problem of product instability, it may be necessary to isolate mutations in other protease genes to obtain maximum product stability.

In addition to using mutants of *B. subtilis*, the onset of endospore development and the secretion of proteases can be reduced significantly simply by adding to the medium a substance, such as glucose, which blocks the onset of secondary metabolism (Hoch, 1976). In the presence of glucose, the secretion of many proteases and cell lysis are inhibited. Cell lysis is to be avoided since release of intracellular proteins, of which some could be proteases, could result in additional degradation of the product and make it more difficult and costly to purify.

We have now discovered a new method for microbial production and export of a desired protein which avoids some of the problems associated with secretion via a signal peptide and secretion during stationary phase of growth. The method of this invention results in the transport of protein out of a flagellated bacterium and does so during the logarithmic growth phase and in the presence of a repressive substance such as glucose. Products thus secreted are likely to be spared the problem of degradation by some proteases. Combining this secretion method with protease deficient mutants may improve product stability even more. This method harnesses the export system normally used by the host cell in exporting the protein flagellin.

Before describing the subject invention in detail, it may be helpful to set forth briefly further background information concerning flagellin.

Flagellin, which is the monomeric protein component of the flgellar filament, is a major extracellular protein product in many bacteria. Specifically, it is the predominant extracellular protein in logarithmic and early stationary phase of growth when Bacillus is grown in minimal salts and glucose. The mechanism by which flagellin is exported is unknown. It does not seem to be exported by using a signal sequence which is cleaved from the amino-terminus of the protein (Silhavy et al., 1983). The amino-terminus of purified flagellin from *Caulobacter crescentus*, for example, has a sequence which corresponds to the putative translation start of its cloned structural gene (Gill and Aggbian, 1982, 1983). The amino-terminus of purified flagellin from *Salmonella typhimurium* begins with alanine which corresponds to the second amino acid following the translation start of its cloned structural gene (Joys and Rankis, 1972; Zieg and Simon, 1980). It is therefore unlikely that a processed leader sequence mediates transport of flagellin in bacteria such as Bacillus, Salmonella or Caulobacter.

Flagellin and several other proteins seem to exit the cell through the central core of the flagellum (Iino, 1977; Silverman and Simon, 1977). These proteins can be as large as about 60 Kd so the physical size of the organelle core does not seem to limit this system unduly. The mechanism of secretion and the structural necessities of proteins to be exported by this system are not known, but much information about this system and the related system in *E. coli* has been collected and reviewed by Iino (1977) and Silverman and Simon (1977). One notable feature of the system is its efficiency. It suffices to note that a flagellated *E. coli* cell has some 60,000 flagellin molecules (Komeda, 1982), thus a culture containing $1\times10^9$ cells per ml exports approximately 5 mg per liter of flagellin.

To date, a minimum of 40 genes have been identified in *E. coli* which are apparently involved in bacterial motility and 29 involved in the synthesis of the flagellar organelle (Iino, 1977; Silverman and Simon, 1977). A pathway for the assembly of a flagellum was proposed by Suzuki and Komeda (1981). The central dogma in flagellar assembly is that the structure is assembled from the cell membrane outward and the new components are derived from proteins that are transported through the core of the organelle and are assembled on the tip of the growing organelle. The flagellin structural gene is one of the last flagellar genes to be transcribed and translated during the synthesis of the flagellar organelle. Thus, a strain deleted for the flagellin gene should have an intact basal body and hook structure but would lack the filament. A mutation of interest to this invention is the cfs mutation, which has a phenotype of constitutive flagellar synthesis when this strain is grown in the presence of glucose (Silverman and Simon, 1977). *E. coli* strains carrying this particular mutation also produce five-fold mre flagellin than wild-type strains.

Grant and Simon, (1969), isolated temperature sensitive (ts)fla mutants of *B. subtilis* 1968 by isolating mutants resistant to bacteriophage PBS1 at high but now at lower temperatures. To date, 3 alleles of the hag locus (encoding the so-called "h-antigen" which is the flagellin protein) in *B. subtilis* have been described. Wild-type *B. subtilis* 168 contains the hag-1 allele, *B. subtilis* W23 has hag-2, and hag-3 is a "straight" mutant of hag-1. Another mutation of interest to this invention is the ifm mutation, which has a phenotype of higher motility and increased flagellin production (Grant and Simon, 1969; Pooley and Karamata, 1984).

In reducing to practice the present invention we have isolated and determined the sequence of the *B. subtilis hag* gene; deleted, in certain embodiments, part or all of this gene from the genome of the host cell; identified essential elements of the sequence involved in transport of the protein to the outside of the cell; inserted into the host cell a heterologous gene encoding a desired protein at some site within the genome of the bacterium or within a flagellin gene locus of the host cell genome or as an extrachromosomal plasmid and expressed and exported fusion proteins containing the desired protein fused to that portion of flagellin essential for export. Methods and materials for the execution of this strategy are disclosed in detail hereinafter.

SUMMARY OF THE INVENTION

This invention concerns a method for producing a heterologous protein in a bacterial host cel such that the protein is exported from the host cell into the culture medium. The method involves culturing in a bacterial culture medium a genetically engineered bacterial strain containing a fusion DNA sequence comprising a first nucleotide sequence encoding at least an N-terminal portion of a flagellin protein and a second nucleotide sequence encoding the heterologous protein. The first nucleotide sequence is linked via its 3' terminus to the 5' terminus of the second nucleotide sequence, and the fusion DNA sequence is itself operatively linked to an expression control sequence. The two linked nucleotide sequences making up the fusion DNA sequence are linked to each other "in frame" such that the coding region of the entire fusion DNA sequece is translated to produce the encoded protein. In certain embodiments the first and second nucleotide sequences are linked by means of a linking nucleotide sequence encoding a selectively cleavable polypeptide. In those embodiments the resulting exported fusion protein may be selectively cleaved by chemical or enzymatic methods to produce the heterologous protein encoded for by the second nucleotide sequence of the fusion DNA sequence. The heterologous protein may then be separately recovered from any polypeptide fragment of flagellin or other proteinaceous material.

BRIEF DESCRIPTION OF THE TABLES AND FIGURES

FIG. 1 depicts restriction maps of clones p4A and p8A and the extent of nucleotide sequencing of clone p4A.

Table 1 depicts the available nucleotide sequence data for clone p4A.

Table 2 depicts the nucleotide and amino acid sequence of the Δ5M proinsulin gene and corresponding protein.

Table 3 depicts the nucleotide sequence of the *E. coli* flagellin gene.

DETAILED DESCRIPTION OF THE INVENTION

The invention relates to a method for producing a heterologous protein in a bacterium of a flagellate species such that the heterologous protein is exported by the bacterium into the bacterial growth medium. The method involves culturing in a suitable bacterial growth medium a bacterial strain containing as part of its genetic material a "fusion" DNA sequence which includes a nucleotide sequence encoding at least a portion of the N-terminus of a flagellin protein linked to a heterologous gene, i.e., a gene encoding a protein other than flagellin. The fusion DNA sequence is operatively linked to an expression control sequence, preferably that of the flagellin gene of the host bacterium, and contains a translational terminating signal 3' to the heterologous gene component.

Suitable host cells may be selected from a wide range of flagellate bacterial species including for example *Escherichia coli*, *Caulobacter crescentus* and *Bacillus subtilis*. The host cell must contain a known or identifiable nucleotide sequence encoding a flagellin protein. It should be noted that bacteria in which flagellin-encoding DNA has not been identified heretofore may also be useful in the practice of this invention. In that case the appropriate nucleotide sequence may be identified and characterized by using conventional techniques to recover and appropriately purify a suitable amoiunt of flagellin from the bacteria for protein sequencing, determine the amino acid sequence of a portion of the flagellin, prepare oligonucleotide probes corresponding to the amino acid sequence so determined, screen a DNA library derived from the bacteria for the presence of a nucleotide sequence capable of hybridizing to the probe(s) and determine the nucleotide sequence of the DNA so identified and/or its location in the bacterial genome. For example, the flagellin gene of *B. subtilis* may be routinely obtained from the *B. subtilis* genome as a 2.5 Kb PstI fragment by purely conventional means using an oligonucleotide probe complementary to part or all of the sequence depicted in Table 1. Similarly, the *E. coli* flagellin gene may be obtained from the *E. coli* Genetic Stock Center, (Barbara Bachmann, Curator, Department of Human Genetics, Yale University, 333 Cedar Street, New Haven, Conn.), on a Clark and Carbon library plasmid, pLC24-16. Part of all of the gene may be routinely identified by hybridization to an oligonucleotide complimentary to the sequence depicted in Table 3.

Preferably, the flagellin gene employed in the practice of this invention should be a native flagellin gene of the bacterial species to be used for expression. However, in certain embodiments the flagellin gene may be derived from a bacterial species different from that of the cells to be used for expression. Thus an *E. coli* flagellin gene may be utilized with a *B. subtilis* host cell.

The wild-type host cell must contain at least one flagellum and preferably, as in the case *B. subtilis* or *E. coli*, a plurality of flagella. In one embodiment the host cell is an increased flagellin and motility (ifm) strain of *B. subtilis*. Strains carrying ifm mutations produce and export significantly more flagellin than wild-type host cells and may be conveniently obtained by iteratively selecting from cultured colonies these cells which migrate furthest away from the spot of inoculation on a semisolid medium referred to as "motility agar". An ifm strain of *B. subtilis*, for example, has been so obtained which produces and exports about twenty times as much flagellin as does the wild-type *B. subtilis*. After appropriate insertion into the genome of the *B. subtilis ifm* strain of a fusion DNA sequence, as disclosed in detail hereinafter, the genetically engineered ifm strain produced and exported about twenty times as much heterologous protein as a similarly treated wild-type strain.

In the practice of this invention the DNA sequence encoding the N-terminal portion of flagellin, e.g. a portion of the hag gene of *B. subtilis*, is operatively linked to an expression control sequence, including for example, a promoter, a ribosome binding site and a translation start codon. Preferably the expression control sequence used is the host cell's expression control sequence for flagellin.

TABLE 1

```
  1 GATCTCCGCATTATCCTCACAAAAAAAGTGAGGATTTTTTTATTTTTGTATTAACAAAATCAGCAGACAAT
 72 CCGATATTAATGATGTAGCCGGGAGGAGGCGCAAAAGACTCAGCCAGTTACAAAATAAGGGCACAAGGACG fMet Arg Ile Asn His Asn Ile Ala Ala
143 TGCCTTAACAACATATTCAGGGAGGAACAAAACA ATG AGA ATT AAC CAC AAT ATT GCA GCG

Leu Asn Thr Leu Asn Arg Leu Ser Ser Asn Asn Ser Ala Ser Gln Lys Asn Met
204 CTT AAC ACA CTG AAC CGT TTG TCT TCA AAC AAC AGT GCG AGC CAA AAG AAC ATG

Glu Lys Leu Ser Ser Gly Leu Arg Ile Asn Arg Ala Gly Asp Asp Ala Ala Gly
258 GAG AAA CTT TCT TCA GGT CTT CGC ATC AAC CGT GCG GGA GAT GAC GCA GCA GGT

Leu Ala Ile Ser Glu Lys Met Arg Gly Gln Ile Arg Gly Leu Glu Met Ala Ser
312 CTT GCG ATC TCT GAA AAA ATG ACA GGA CAA ATC AGA GGT CTT GAA ATG GCT TCT

Lys Asn Ser Gln Asp Gly Ile Ser Leu Ile Gln Thr Ala Glu Gly Ala Leu Thr
366 AAA AAC TCT CAA GAC GGA ATC TCT CTT ATC CAA ACA GCT GAG GGT GCA TTA ACT

Glu Thr His Ala Ile Leu Gln Arg Val Arg Glu Leu Val Val Gln Ala Gly Asn
420 GAA ACT CAT GCG ATC CTT CAA CGT GTT CGT GAG CTA GTT GTT CAA GCT GGA AAC

Thr Gly Thr Gln Asp Lys Ala Thr Asp Leu Gln Ser Ile Gln Asp Glu Ile Ser
474 ACT GGA ACT CAG GAC AAA GCA ACT GAT TTG CAA TCT ATT CAA GAT GAA ATT TCA

Ala Leu Thr Asp Glu Ile Asp Gly Ile Ser Asn Arg Thr Glu Phe Asn Gln Lys
528 GCT TTA ACA GAT GAA ATC GAT GGT ATT TCA AAT CGT ACA GAA TTC AAT GGT AAG

Lya Leu Leu Asp Gly Thr Thr Lys Val Asp Thr Ala Thr Pro Ala Asn Gln Lys
582 AAA TTG CTC GAT GGC ACT TAC AAA GTT GAC ACA GCT ACT CCT GCA AAT CAA AAG

Asn Leu Val Phe Gln Ile Gly Ala Asn Ala Thr Gln Gln Ile Ser Val Asn Ile
636 AAC TTG GTA TTC CAA ATC GGA GCA AAT GCT ACA GAC CAA ATC TCT GTA AAT ATT

Glu Asp Met Gly Ala Asp Ala Leu Gly Ile Lys Glu Ala Asp Gly Ser Ile Ala
690 GAG GAT ATG GGT GCT GAC GCT CTT GGA ATT AAA GAA GCT GAT GGT TCA ATT GCA

Ala Leu His Ser Val Asn Asp Leu Asp Val Thr Lys Phe Ala Asp Asn Ala Ala
744 GCT CTT CAT TCA GTT AAT GAT CTT GAC GTA ACA AAA TTC GCA GAT AAT GCA GCA

Asp Thr Ala Asp Ile Gly Phe Asp Ala Gln Leu Lys Val Val Asp Glu Ala Ile
798 GAT ACT GCT GAT ATC GGT TTC GAT GCT CAA TTG AAA GTT GTT GAT GAA GCG ATC

Asn Gln Val Ser Ser Gln Arg Ala Lys Leu Gly Ala Val Gln Asn Arg Leu Glu
852 AAC CAA GTT TCT TCT CAA CGT GCT AAG CTT GGT GCG GTA CAA AAT CGT CTA GAG
```

TABLE 1-continued

|  | His | Thr | Ile | Asn | Asn | Leu | Ser | Ala | Ser | Gly | Glu | Asn | Leu | Thr | Ala | Ala | Glu | Ser |
|---|---|---|---|---|---|---|---|---|---|---|---|---|---|---|---|---|---|---|
| 906 | CAC | ACA | ATT | AAC | AAC | TTA | AGC | GCT | TCT | GGT | GAA | AAC | TTG | ACA | GCT | GCT | GAG | TCT |

|  | Arg | Ile | Arg | Asp | Val | Asp | Met | Ala | Lys | Glu | Met | Ser | Glu | Phe | Thr | Lys | Asn | Asn |
|---|---|---|---|---|---|---|---|---|---|---|---|---|---|---|---|---|---|---|
| 960 | CGT | ATC | CGT | GAC | GTT | GAC | ATG | GCT | AAA | GAG | ATG | AGC | GAA | TTC | ACA | AAG | AAC | AAC |

|  | Ile | Leu | Ser | Gln | Ala | Ser | Gln | Ala | Met | Leu | Ala | Gln | Ala | Asn | Gln | Gln | Pro | Gln |
|---|---|---|---|---|---|---|---|---|---|---|---|---|---|---|---|---|---|---|
| 1014 | ATT | CTT | TCT | CAG | GCT | TCT | CAA | GCT | ATG | CTT | GCT | CAA | GCA | AAC | CAA | CAG | CCG | CAA |

|  | Asn | Val | Leu | Gln | Leu | Leu | Arg | Oc |
|---|---|---|---|---|---|---|---|---|
| 1068 | AAC | GTA | CTT | CAA | TTA | TTA | CGT | TTA | TTTTAAAAAAGACCTTGGCGTTGCCAGGGTCTTTTAATT |
| 1131 | TAAATTTCTATCTCCTAATCATTCCTCATCCTGTCACTAACTCATGATATAATAACCGGATTCTCCACTAA |
| 1202 | CTTTTTATAAATGTATTTCCATACAAGAAATCTAAAACAGAAGATTTTTTTCCAAAAATATGTGTAATCTT |
| 1273 | ATCTCGACTTAGTCGATATAAACGATAGATTGGGGCATAGGGGATGATCAATTGAACATTGAAAGGCTCAC |
| 1344 | TACGTTACAACCTGTTTGGGATCGTTATGATACTCAAATACATAATCAGAAAGATAATGATAACGAGGTTC |
| 1415 | CTGTTCATCAAGTTTCATATACCAATCTTGCTGAAATGGTGGGGGAAATGAACAAGCTT |

TABLE 3 flagellin coding sequence is underlined

| 1 | ccgactccc | agcgatgaaa | tacttgccat | gcgatttcct | tttatctttc |
|---|---|---|---|---|---|
| 51 | gacacgtaaa | acgaataccg | ggttatcgg | tctgaattgc | gcaaagttta |
| 101 | gctttaattg | ttttttttaa | tagcgggaat | aaggggcaga | gaaaagagta |
| 151 | tttcggcgac | taacaaaaaa | tggctgtttt | tgaaaaaaat | tctaaaggtt |
| 201 | gttttacgac | agacgataac | agggttgacg | gcgattgagc | cgacgggtgg |
| 251 | aaacccaata | cgtaatcaac | gacttgcaat | ataggataac | gaatcatgga |
| 301 | acaagtcatt | aataccaaca | gcctctcgct | gatcactcaa | aataatatca |
| 351 | acaagaacca | gtctgcgctg | tcgagttcta | tcgagcgtct | gtcttctggc |
| 401 | ttgcgtatta | acagcgcgaa | ggatgacgca | gcgggtcagg | cgattgctaa |
| 451 | ccgtttcacc | tctaacatta | aaggcctgac | tcaggcgcc | cgtaacgcca |
| 501 | acgacggtat | ctccgttgcg | cagaccacca | ccgaaggcgc | gctgtccgaa |
| 551 | atcaacaaca | acttacagcg | tgtgcgtgaa | ctgacggtac | aggccactac |
| 601 | cggtactaac | tctgagtctg | atctgtcttc | tatccaggac | gaaattaaat |
| 651 | cccgtctgga | tgaaattgac | cgcgtatctg | gtcagaccca | gttcaacggc |
| 701 | gtgaacgtgc | tggcaaaaaa | tggctccatg | aaaatccagg | ttggcgcaaa |
| 751 | tgataaccag | actatcacta | tcgatctgaa | gcagattgat | gctaaaactc |
| 801 | ttggccttga | tggttttagc | gttaaaaata | acgatacagt | taccactagt |
| 851 | gctccagtaa | ctgcttttgg | tgctaccacc | acaaacaata | ttaaacttac |
| 901 | tggaattacc | ctttctacgg | aagcagccac | tgatactggc | ggaactaacc |
| 951 | cagcttcaat | tgagggtgtt | tatactgata | atggtaatga | ttactatgcg |
| 1001 | aaaatcaccg | gtggtgataa | cgatgggaag | tattacgcag | taacagttgc |
| 1051 | taatgatggt | acagtgacaa | tggcgactgg | agcaacggca | aatgcaactg |
| 1101 | taactgatgc | aaatactact | aaagctacaa | ctatcacttc | aggcggtaca |
| 1151 | cctgttcaga | ttgataatac | tgcaggttcc | gcaactgcca | accttggtgc |
| 1201 | tgttagctta | gtaaaactgc | aggattccaa | gggtaatgat | accgatacat |
| 1251 | atgcgcttaa | agatacaaat | ggcaatcttt | acgctgcgga | tgtgaatgaa |
| 1301 | actactggtg | ctgtttctgt | taaaactatt | acctatactg | actcttccgg |
| 1351 | tgccgccagt | tctccaaccg | cggtcaaact | gggcggagat | gatggcaaaa |
| 1401 | cagaagtggt | cgatattgat | ggtaaaacat | acgattctgc | cgatttaaat |
| 1451 | ggcggtaatc | tgcaaacagg | tttgactgct | ggtggtgagg | ctctgactgc |
| 1501 | tgttgcaaat | ggtaaaacca | cggatccgct | gaaagcgctg | gacgatgcta |
| 1551 | tcgcatctgt | agacaaattc | cgttcttccc | tcggtgcggt | gcaaaaccgt |
| 1601 | ctggattccg | cggttaccaa | cctgaacaac | accactacca | acctgtctga |
| 1651 | agcgcagtcc | cgtattcagg | acgccgacta | tgcgaccgaa | gtgtccaatc |
| 1701 | tgtcgaaagc | gcagatcatc | cagcaggccg | gtaactccgt | gttggcaaaa |
| 1751 | gctaaccagg | taccgcagca | ggttctgtct | ctgctgcagg | gttaatcgtt |
| 1801 | gtaacctgat | taactgagac | tgacggcaac | gcaaattgcc | tgatgcgctg |
| 1851 | cgcttatcag | gcctacaagt | tgaattgcaa | tttattgaat | ttgcacattt |
| 1901 | ttgtaggccg | gataaggcgt | ttacgcgcat | ccggcaacat | aaagcgcaat |
| 1951 | ttgtcagcaa | cgtgcttccc | gccaccggcg | gggtttttt | ctgcctggaa |
| 2001 | tttacctgta | accccaaat | aaccctcat | ttcacccact | aatcgtccga |
| 2051 | ttaaaaccc | tgcagaaacg | gataatcatg | ccgataactg | ctataacgca |
| 2101 | gggctgttt | | | | |

Thus in the ifm embodiment the preferred expression control sequence is the expression control sequence of the hag gene.

Depending on the amount and nature of flagellin DNA which is fused to, the heterologous gene, the heterologous protein which is produced and exported will usually be a fusion protein comprising at least a portion of the flagellin protein linked to the protein encoded for by the heterologous gene. In certain embodiments of the invention the fusion DNA sequence contains a full-length flagellin-encoding nucleotide sequence linked via its 3' terminus to the 5' terminus of the heterologous gene. In other embodiments the flagellin-encoding sequence is truncated at its 3' terminus. Thus, in one embodiment the fusion DNA sequence contains nucleotides 1-633 of the flagellin-encoding gene linked via nucleotide 633 to the 5' terminus of the heterologous sequence. In another embodiment a shorter portion of the flagellin gene is used which contains nucleotides 1-432. Other embodiments may contain deletions of various lengths within the 432-912 nucleotide region of the flagellin gene. Sequences containing further deletion of nucleotides 5' to nucleotide 432 are also expected to be useful in the practice of this invention although the exact length of the remaining flagellin sequence which permits or optimizes export of the fusion protein has not yet been precisely determined. Indeed, in specific cases the desired flagellin-encoding sequence may be only about 75, 50, 25 or 10 codons in length. Even shorter flagellin-encoding sequences may be useful in this invention, and it is possible that the 5' untranslated region alone of the flagellin gene, with no flagellin-encoding nucleotide sequence, will permit export of the heterologous protein in certain cases. By "heterologous" as the term is used herein is meant a protein or DNA sequence other than a flagellin protein or a DNA sequence encoding a flagellin protein, respectively.

In one embodiment the fusion DNA sequence contains an additional nucleotide sequence which links the flagellin gene portion and the heterologous gene. Preferably the linking sequence encodes a polypeptide which is selectably cleavable or digestable by conventional chemical or enzymatic methods. The fusion protein of this embodiment will thus contain an engineered cleavage site at which it may be selectively cleaved. Cleavage of the fusion protein yields the "mature" protein which is encoded by the heterologous gene. The mature protein may in turn be obtained in purified form, free from any polypeptide fragment of flagellin to which it was previously linked.

Preferably, the engineered host cells produce and export the heterologous protein during a growth phase when protease secretion is at a minimum. Such is the case with *B. subtilis,* in which production and export of the heterologous protein occurs during the logarithmic/early stationary growth phase. It is also preferred that the engineered host cells produce and export the heterologous protein in the presence of a substance which tends to further reduce the level of exported proteases e.g. glucose, in the case of *B. subtilis.*

As this invention is not limited to any specific type of heterologous DNA a wide variety of heterologous proteins may be produced by this method including, for example, proteins useful for human or veterinary therapy or diagnostic applications, such as hormones, cytoxins, growth or inhibitory factors, etc., enzymes, and modified natural or wholly synthetic proteins.

Furthermore, it should be understood that a variety of recombinant genetic constructions will be useful in achieving the primary objective of this invention, namely the utilization of the bacterial machinery normally used in the bacterial production and export of flagellin to effect the production and export of a heterologous protein from a flagellate bacterium. Indeed, several illustrative recombinant approaches are presented hereinafter. Accordingly, it should also be understood that this invention is not limited to any one particular recombinant method for achieving its objectives.

One approach for producing a genetically engineered bacterium of this invention involves deleting a portion or all of the flagellin gene from the chromosome of the host bacterium and inserting into the flagellin deletion locus or into another chromosomal locus, a plasmid-born heterologous gene via a single recombination event. The replacement of the host flagellin gene with a deleted version constructed in vitro is performed by established methods (Stahl and Ferarri, 1984, Yang et al., 1984; Kawamura and Doi, 1984). The use of an "integrable plasmid" or an "integration vector" in *B. subtilis* is well documented (Ferrari et al., 1983). This particular integration vector is comprised of a selectable antibiotic resistance gene and a plasmid origin that allows extrchromosal replication in *E. coli,* but not in *B. subtilis.* In addition, this vector must include a sequence which is homologous to a sequence within the host genome; this may be a portion of the flagellin gene that has not been deleted from the host genome, or the sequence could be a portion or all of another host gene. The plasmid also includes a heterologous gene fused to a portion of the flagellin gene to allow expression and export of a heterologous protein. When an integration vector such as described above is transformed in *B. subtilis,* transformed cells carrying the plasmid-borne antibiotic resistance gene are selected. This plasmid cannot replicate extrachromosomally, therefore the plasmid integrates into the genome via a single recombination event between the homologous sequences on the plasmid and the chromosome. The resulting chromosomal structure contains the plasmid flanked by directly duplicated copies of the homologous sequence. As long as antibiotic selection is maintained, the plasmid-derived sequences are replicated and stably inherited as part of the bacterial genome. In some cases, perhaps depending on which antibiotic resistance gene is placed on this plasmid, the integrated plasmid can be "amplified", or the number of integrated plasmid copies can be increased, by growth of the strain carrying the integrated plasmid in higher levels of the antibiotic used to select for the initial integration (Gutterson and Koshland, 1983). This results in amplification of the number of heterologous gene copies which may result in increased expression and export of heterologous protein. Further increases in expression and export of heterologous protein may be accomplished by transforming, with or without amplification, the plasmid into a host strain carrying the ifm mutation.

A second approach involves stably inserting a plasmid into a flagellin deletion strain, preferably one that contains the ifm mutation, wherein the plasmid contains a fusion DNA sequence as previously described and in addition, a functional origin that allows extrachromosomal replication in *B. subtilis.* The plasmid must also contain a selectable gene, such as an antibiotic resistance gene, which can be used to select for the inheritance of the plasmid by transformation and to insure maintenance of the plasmid during culture growth. To maximize the expression and export of heterologous protein, it may be useful to adjust heterologous gene dosage, or copy number, by placing the gene into the different plasmids. For example, the plasmid pUB110, which is a *Staphylococcus aureus* plasmid that is often used in *B. subtilis* molecular biological applications, is a potentially useful high copy number plasmid (Gryczan, et al., 1978). This particular plasmid has a copy number of approximately 40 per cell. Another plasmid, pE194, may be useful as a low copy plasmid in *B. subtilis* (Gryczan and Dubnau, 1978). When this plasmid is transformed into *B. subtilis* it maintains a copy number of approximately 5-10 per cell.

A third approach for producing a genetically engineered bacterium of this invention is to integrate a plasmid, which is comprised of a heterologous gene fused to the 3' end of a portion of the flagellin gene that lacks the transcription and translation control sequence and in addition may lack a portion of the gene encoding the N-terminal region of the gene, into a B. subtilis host containing an intact flagellin gene and preferably the ifm mutation. This integrable plasmid also contains a selectable antibiotic resistance gene and a plasmid origin that allows extrachromosomal replication in E.coli, but not in B. subtilis. When transformed into B. subtilis, selection is for the inheritance of the antibiotic resistance gene and integration into the chromosome is mediated by a single recombination event between the flagellin sequence on the plasmid and the corresponding homologous sequence within the flagellin gene in the chromosome. As a result of integration, the heterologous gene is fused to the transcription and translation regulatory sequences and all or part of the encoding sequences of the host flagellin gene. The fusion junction between flagellin and the heterologous gene must be a codon that is 3' of those flagellin sequences required for export. If so, the integration of this plasmid generates one copy of a completely functional gene that codes for the expression and export of a heterologous protein. The integration also generated two truncated and nonfunctional genes, a flagellin gene that lacks transcription and translation control sequences and may or may not contain sequences encoding for a portion of the N-terminus, and a flagellin-heterologous gene fusion that lacks the same sequences. With this particular integration scheme the latter truncated gene may be amplified by amplifying the plasmid sequences. Thus transformation of this plasmid into B. subtilis interrupts the host flagellin gene and at the same time introduces the desired gene fusion between flagellin and the heterologous gene at a copy number of one per chromosome.

Numerous aspects and advantages of the invention will be apparent to those skilled in the art upon consideration of the preceding in view of the illustrative experimental examples, results, and discussion which follow.

EXPERIMENTAL EXAMPLES

Materials and Methods

Bacterial strains and plasmids.

Escherichia coli MM294 (F−, supE44, endA1, thi-1, hsdR4) was used as a host for plasmid constructions and for screening the pUC 18 based Bacillus subtilis 168 genomic library. E. coli was transformed by the procedure of Dagert and Ehrlich (1979), with selection or L agar plates containing 15 μg/ml neomycin, 15 μg/ml chloramphenicol, or 50 μg/ml ampicillin. B. subtilis strains were transformed by the procedure of Anagnostopoulos and Spizizen (1961), with selection on L agar plates containing 5 μg/ml neomycin or 5 μg/ml chloramphenicol. Auxotrophic markers were selected on minimal glucose plates supplemented with the appropriate amino acids at 50 μg/ml (Spizizen, 1958). B. subtilis G1B1 was constructed by transforming B. subtilis 168 trpC2 with B. subtilis W23 DNA and selecting for Trp+ transformants. An ifm mutation was selected in this strain by repeated selection for hypermotility on motility agar by the method of Grant and Simon (1969).

The plasmids pBR322, pJH101, pUC18, pUC19, and pUB110 have all been described previously (Bolivar, et al., 1979; Yanisch-Perron et al., 1985; Ferrari et al., 1983; Gryczan et al., 1978). The plasmid pAIΔ5M contains the human proinsulin gene that has been specifically mutagenized to encode a proinsulin that can be processed in vitro to insulin by enzymatic and chemical means (U.S. Ser. No. 646,573 and International Application No. PCT/US85/01673; see FIG. 3).

Reagents and media

Restriction enzymes, T4 polynucleotide kinase, Bal-31 exonuclease, and the Klenow fragment of E. coli DNA polymerase I were purchased from commercial sources and used according to the suppliers' conditions. Motility deficient mutants were screened and tested on motility agar (Grant and Simon, 1969). For the expression and export of homologous and heterologous proteins, cultures were grown in expression medium, which contained minimal salts (Spizizen, 1958) supplemented with 2% glucose, 0.1% technical grade casamino acids (Difco), and the appropriate amino acids supplemented at 50 μg/ml. In some experiments, total protein was labeled with L-[$^{35}$S]-methionine (>400 Ci/mmol; New England Nuclear) by addng 10 μCi/ml to the above medium.

DNA and protein characterization

Plasmid DNA was prepared from E. coli transformants by the alkaline lysis method of Birnboim and Doly (1979). B. subtilis chromosomal DNA was prepared by the method of Marmur (1961). The separation of retriction fragments on polyacrylamide and agarose gels and the electroelution of DNA fragments were performed as previously described (Lawn et al., 1981). All plasmid constructions were made with DNA fragments purified by electroelution from gels. Restriction fragments were ligated into appropriate sites of M13 phage vectors mp18 or mp19 (Vieira and Messing, 1982; Yanisch-Perron et al., 1985) in preparation for sequence determination by dideoxy methods (Sanger et al., 1977). DNA restrictionf fragments were prepared as probes by labeling [alpha-$^{32}$P] CTP by nick-translation (Rigby et al., 1971). Synthetic oligonucleotides were synthesized by the phosphotriester method (Crea and Horn, 1980), and end labeled with [gamma-$^{32}$P] ATP and T4 polynucleotide kinase (Richardson, 1971). Hybridization conditions for the labeled oligonucleotide pools were at 37° C. in a solution of 1X Denhardt solution, 0.1 mM ATP, 1 mM NaCl, 0.5% Nonidet ® P-40, (a nonionic detergent; Sigma), 200 ng/ml soluble type XI bakers yeast RNA (Sigma), 90 mM Tris-OH pH 7.5, and 6 mM EDTA. Washing was at 37° C. in 6X SSC (1X SSC is 0.15M NaCl plus 0.015 M sodium citrate). For southern hybridization analysis, digested DNA fragments were separated on 1% agarose and depurinated as described by Wahl et al. (1979) and transferred to nitrocellulose by the method of Southern (1975). Hybridizations and washings for southern blots with nick-translated probes were performed as described by Maniatis et al. (1978).

For the expression and export of homologous or heterologous proteins, isolated colonies were picked from streak plates or transformation plates and inoculated into expression medium with or without L-$^{35}$S-methionine. The culture was grown to mid-logarithmic stage of growth (OD$_{550\,nm}$=0.5) and at this time phenylmethylsulfonyl fluoride (PMSF) and EDTA were added to the culture each at final concentrations of 1 mM. PMSF and EDTA are serine protease and metalloprotease inhibitors respectively and their addition increases the stability of heterologous proteins in the medium. One hour after the addition of the protease inhibitors one ml aliquots were removed; if the stain being examined contains the wild-type flagellin gene intact, the culture sample is heated at 80° C. for 10 min to depolymerize the flagellar filament into flagellin monomers; if a flagellin-heterologous fusion protein is being expressed and exported, the heat treatment is not needed. The culture aliquot is then centrifuged for 3 minutes in an Eppendorf centrifuge, in 1.5 ml eppendorf tubes, and 900 μL of supernatant is removed and added to another tube containing 100 μL of 100% trichloroacetic acid (TCA). The TCA precipitations were allowed for 20 min. on ice, then are centrifuged for 5 min. and the pellet washed three times with one ml aliquots of cold acetone. The cell pellet was washed in one ml of wash buffer (100 mM tris pH8, 150 mM NaCl, 1 mM EDTA) and resuspended in 50 μL of TE buffer (10 mM tris pH 8, 1 mM EDTA). The cells were then lysed by sonic disruption. The proteins from the cell pellet and supernatant fractions were then separated on SDS-polyacrylamide gels according to Laemmli (1970) and transferred to nitrocellulose electrophoretically for western blot analysis by the method of Burnette (1981).

B.subtilis 168 flagellin was purified by the method of Martinez (1963). Once isolated, the material was separated from minor contaminants on a preparative SDS-polyacrylamide gel and the band cntaining flagellin was cut out lyophilzed and used as an antigen in rabbits for the production of flagellin specific antibodies. This protocol resulted in the production of highly specific antibodies for the detection of flagellin and flagellin-heterologous fusion proteins by western blot analysis.

RESULTS

Characterization of the ifm mutation.

B. subtilis G1B1 and B. subtilis G1B1 ifm were grown in expression medium plus L-$^{35}$S-methionine to mid-logarithmic phase of growth. Samples from the culture were processed as described in the methods section to compare the levels of flagellin produced in the two strains. There was approximately 10-fold more flagellin exported in the stain carrying the ifm mutation. The western blot with antiflagellin antibody confirmed that this protein is flagellin.

Cloning of the B. subtilis hag gene.

The 17-mer oligonucleotide probe pool for the cloning, by hybridization, of the hag gene of B. subtilis G1B1 was designed and based on the published amino acid sequence of flagellin (Delange et al., 1976). Two pools of 12 17-mer oligonucleotides completely covered the degeneracy of amino acids 170-174 and, in addition, the first two bases of the glycine codon at amino acid 175 of the sequence (Asn-Ile-Glu-Asp-Met-Gly). The sequences of the oligonucleotides in pool number 1 are 5'-A-A-T/C-A-T-T/C-A-G-A-A/G-G-A-T-AT-G-G-G-3' and pool number 2 are 5'-A-A-T/C-A-T-T/C-A-G-A-A/G-G-A-C-A-T-G-G-G-3'.

A genomic library was prepared in pUC18 using DNA from B. subtilis G1B1. The vector was digested with SalI and the first two bases complementary to the 5' overlapped ends were filled in using the Klenow fragment of DNA polymerase I and dTTP and dCTP. The bacterial DNA was partially digested with Sau3A and sized on a preparative agarose gel. DNA fragments ranging in size from 2-5 Kb were cut out and electroeluted from the gel and then treated with the Klenow fragment and dGTP and dATP to fill in the first two bases complementary to the overlapped ends. The insert and vector DNAs were then ligated with T4 DNA ligase. This strategy allowed only one insert per vector and prevented tandem ligations of two or more insert DNA fragments or religation of vector DNA fragments (Hung and Wensik, 1984). E.coli MM294 was transformed with the above ligated DNA and the screening of bacterial colonies for plasmids with inserts containing the flagellin gene was by transfer to nitrocellulose according to Grunstein and Hogness (1975). Crude restriction maps of two clones identified as hybridization positives, p4A and p8A, are shown in FIG. 1. The complete sequence of an open reading frame contained in both p4A and p8A was found to encode a protein that is 304 amino acids; all but two amino acids are homologous to the published protein sequence of B. subtilis 168 flagellin (Delange et al., 1976; 1). The exception was a pair of amino acids, glycine-101 and threonine-102, which are inverted in the published sequence. The extent of clone p4A that is sequenced is shown in FIG. 1 and the sequence itself is shown in Table 1.

Construction of E. coli-B. subtilis shuttle vectors.

The E. coli-B. subtilis shuttle vector, pBE3, contains the pUC18 polylinker (147 bp EcoRI-PvuII restriction fragment), the pBR322 origin of replication (1166 bp PvuII-AhaIII restriction fragment), and the neomycin nucleotidyl transferase gene and origin of replication from pUB110 (3,529 bp PvuII-EcoRI restriction fragment). The order of these fragments in a clockwise direction n a circular map is EcoRI--polylinker--PvuII/PvuII--pBR322 origin--AhaIII/PvuII--pUB110 origin--neomycin gene--EcoRI. This plasmid replicates autonomously and confers neomycin resistance in both E. coli and B. subtilis.

The integration vector, pIEV1, is a derivative of pJH101 that replicates autonomously in E. coli, but when transformed into B. subtilis, must integrate into the chromosomal flagellin locus. The plasmid contains the chloramphenicol acetyl transferase (CAT) gene and origin of replication from pJH101 (3,224 bp PstI-AvaI restriction fragment), part of the pUC18 polylinker (200 bp PvuII-XbaI restriction fragment) and a 400 bp HindIII-PstI restriction fragment from the B. subtilis chromosome just 5' of the hag promoter region (see FIG. 1). The 5' overlaps of the AvaI, XbaI, and HindIII ends were filled in by the Klenow fragment of DNA pol I with all four dNTPs before ligation. The order of these restriction fragments in a clockwise direction on a circular map is PstI--origin-CAT gene--AvaI/PvuII-polylinker-XbaI/HindIII--400 bp chromosome fragment--PstI.

Construction of pIEV1fla304PIΔC.

The plasmid pIEV1fla304PIΔC is a derivative of plasmids, pBE3, pALIΔ5M, p4A, and pIEV1 which contains the pBR322 origin of replication, the CAT gene which confers functional resistance to chloramphenicol in both E. coli and B. subtilis, and a sequence which encodes amino acids 144–304 of flagellin (see Table 1), four junction amino acids (Gly-Met-Gln-Ala), and the Δ5M proinsulin gene (see Table 2). The latter encoding sequence does not contain regulatory sequences for the initiation of transcription and translation. When transformed into B. subtilis G1B1 ifm, it integrates via a single recombination event between the homologous plasmid-borne and chromosomal flagellin sequences and results in the reconstitution of a functional gene which encodes a fusion protein containing 1–304 amino acids of flagellin, the 4 junction amino acids, and the Δ5M proinsulin sequence. This gene includes the host transcription and translation start sequences of the flagellin gene.

DISCUSSION

TABLE 2

| | Met | Phe | Val | Asn | Gln | His | Leu | Cys | Gly | Ser | His | Leu | Val | Glu | Ala | Leu | Tyr | Leu |
|---|---|---|---|---|---|---|---|---|---|---|---|---|---|---|---|---|---|---|
| 1 | ATG | TTT | GTG | AAC | CAA | CAC | CTG | TGC | GGC | TCA | CAC | CTG | GTG | GAA | GCT | CTC | TAC | CTA |
| | Val | Cys | Gly | Glu | Arg | Gly | Phe | Phe | Tyr | Thr | Pro | Lys | Thr | Asp | Leu | Gln | Val | Gly |
| 55 | GTG | TGC | GGG | GAA | CGA | GGC | TTC | TTC | TAC | ACA | CCC | AAG | ACC | GAT | CTG | CAG | GTG | GGG |
| | Gln | Val | Glu | Leu | Gly | Gly | Gly | Pro | Gly | Ala | Gly | Ser | Leu | Gln | Pro | Leu | Ala | Leu |
| 109 | CAG | GTG | GAG | CTG | GGC | GGG | GGC | CCT | GGT | GCA | GGC | AGC | CTG | CAG | CCC | TTG | GCC | CTG |
| | Glu | Gly | Ser | Leu | Gln | Lys | Arg | Met | Gly | Ile | Val | Glu | Gln | Cys | Cys | Thr | Ser | Ile |
| 163 | GAG | GGG | TCC | CTG | CAG | AAG | CGT | ATG | GGC | ATT | GTG | GAA | CAA | TGC | TGT | ACC | AGC | ATC |
| | Cys | Ser | Leu | Tyr | Gln | Leu | Gln | Asn | Tyr | Cys | Asn | Am | | | | | | |
| 217 | TGC | TCC | CTC | TAC | CAG | CTG | GAG | AAC | TAC | TGC | AAC | TAG | | | | | | |

This plasmid was constructed as follows. The 4750 bp HindIII-PvuII restriction fragment from pBE3, (the first three bases of the HindIII 5' overlap were filled in by the Klenow fragment with dATP, dGTP, and dCTP), was ligated to the 470 bp SphI-NdeI restriction fragment from pALIΔ5M, (the 3' overlap of the SphI site was chewed back by the Klenow fragment and the first base of the NdeI 5' ovelap was filled in by the Klenow fragment with dTTP), to construct pFPI1. The 5200 bp BamHI-PstI restriction fragment from pFPI1, (the 3' overlap of PStI was removed using the Klenow fragment), was ligated to the 2632 bp BamHI-AhaIII restriction fragment from p4A to construct pFPIfla304. The AhaIII end of the fragment from P4A to construct pFPIfla304. The AhaIII end of the fragment from p4A was treated with "slow"]bal-31 exonuclease before ligation, and the proper pFPIfla304 construction was screened by colony hybridization with an oligonucleotide (50'-T-T-A-T-T-A-C-G-T-G-G-C-A-T-G-C-A-A3') that spans the correct ligation juntion. The sequences of the hybridization positives were determined to confirm the proper construction. The 1621 bp BamHI-BglI restriction fragment friom pFPlfla304, (the BglI 5' overlap was filled in with the Klenow fragment and all four dNTPs), was ligated to the 3727 bp BamHI-ECoRI restriction fragment from pIEV1 (the EcoRi 5' overlap was filled in with the Klenow fragment and all four dNTPs) to construct the plasmid pIEV1fla304PI. The plasmid pIEV1fla304PIΔC was constructed by digesting pIEV1fla304PI with ClaI, purifying the 4500 bp fragment and religating the same fragment.

Expression and export of flagellin-proinsulin fusion protein in B. subtilis G1B1 ifm.

The plasmid pIEV1fla304PIΔC was transformed into B. subtilis G1B1 ifm and an isolated colony was used to inoculate 10 ml of expression medium plus L-[35S]-methionine in a 250 ml baffled erlenmeyer flask. The culture was incubated at 37° C. on a gyratory shaker operating at 250 revolutions per minute. At the mid-logarithmic stage of growth ($OD_{550}$ nm=0.5), protease inhibitors were added and one hour later samples were removed and processed as described in the Methods section. After examination of the $^{35}$S-methionine total labelling and western blot autiradiograms, the flagellin-proinsulin fusion protein was identified as a band that bound antiflagellin antibody and migrated at the expected molecular weight when compared to the migration of flagellin. The appearance of this band in the supernatant fraction of the culture aliquot confirms that a significant amount of flagellin-proinsulin fusion protein was exported into the medium.

Flagellin in B. subtilis G1B1 ifm is exported at levels up to 10–20% of the total cell protein during logarithmic stage of growth, in the presence of glucose, where the secretion of extracellular proteases is minimized. In this invention the flagellin export pathway has been utilized to export heterologous fusion proteins into the culture medium. In a specific demonstration of the potential for this system a recombinant flagellin-proinsulin fusion protein was exported via the flagellin export pathway. This same experimental approach was successfully used to export another flagellin-heterologous fusion protein, namely flagellin-TEM β-lactamase fusions. This particular β-lactamase is from the plasmid pUC18 (Yanisch-Perron et al., 1985), and confers ampicillin resistance to various gram negative bacteria including E. coli. Flagellin-β-lactamase gene fusions were expressed in Bacillus which resulted in the accumulation of flagellin-β-lactamase fusion protein in the culture medium. This fusion protein has β-lactamase activity and also cross reacts with antiflagellin and antiβ-lactamase antibodies. In addition, strains carrying the flagellin-β-lactamase gene fusions were resistant to ampicillin. These results indicate that the flagellin export system may be useful for the production of many homologous and heterologous proteins.

The flagellin-proinsulin fusion protein contains a methionine residue at the junction between the flagellin amino acid residues and the proinsulin residues thus the latter could be cleaved from flagellin with cyanogen bromide. Active and properly folded insulin may thus be obtained by combined treatment of the fusion protein with cyanogen bromide and a specific protease from Psedomonas fragii. Accordingly, the strategy for the export of a variety of homologous or heterologous proteins via the flagellin pathway is to fuse the coding sequence for that protein "X" to a portion or all of the flagellin coding sequence, and at the junction, introduce a specific cleavage site so that the desired sequence may be removed by chemical or enzymatic means. In addition to cyanogen bromide, which cleaves on the carboxy side of the methionine residues, formic acid may be used to cleave between aspartic acid and proline residues (Nilsson et al., 1985). There are highly specific proteases which also may be useful for site specific cleavages. Two examples are porcine enteropeptidase, which cleaves on the carboxy side of the sequence (Asp)$_4$-Lys (Maroux et al., 1971), and factor X$_a$, which cleaves on the carboxy side of the sequence Ile-Glu-Gly-Arg (Nagai and Thogersen, 1984). A nucleotide sequence that encodes for either of the specific recognition sites for these or other specific proteases may be placed, by conventional recombinant methods, at the junction of flagellin-protein "X" encoding sequences. The use of specific proteases and methods known in the art to cleave fusion proteins exported via the flagellin pathway would result in the release of protein "X" without an f-Met or Met residue at the N-terminus.

The fact that export via the flagellin pathway may require a portion or all of the flagellin coding sequence may be advantageous with respect to purification of flagellin-protein "X" fusion proteins. Flagellin can be purified easily and is highly antigenic, consequently fusion proteins may be purified by affinity chromatography with flagellin antibody, then processed by the appropriate chemical or enzymatic means. The fusion proteins may also be purified by purely conventional means or by immunoaffinity chromatography using antibodies directed to the non-flagellin portion of the fusion protein, i.e. the desired protein.

Many homologous or heterologous proteins exported as flagellin fusion proteins would require specific processing to a mature, active form by specific chemical or enzymatic means as described above. Examples of these types of proteins include insulin, colony stimulating factors, human growth hormone, or other pharmaceutical destined for human use. Other proteins, for example, enzymes such as proteases, amylases or proteins such as animal growth hormones, may be active and suitable for use as flagellin fusion proteins. In cases such as these the specific chemical or enzymatic processing step required for removal of the flagellin encoding sequences would be unnecessary.

The export of homologous or heterologous proteins via the flagellin export pathway may be further improved by modifications in host cell development, vectors, and promoter vector combinations. At least two general categories of host cell mutations may further increase the final yield of flagellin-protein "X" fusion protein obtained in this process. To increase the stability of exported proteins in the culture medium, host mutations that decreases protease activity may be used. Most protease activity can be minimized simply by growing the culture in the presence of excess glucose, but further improvements may be obtained by isolating mutations in regulatory genes, such as spoO mutations, which are pleitropic and result in decreased expression of some proteases (Michel and Millet, 1970; Hoch, 1976). Recombinant methods may be used to isolate in vitro-derived mutations in other protease structural genes as has been accomplished with the alkaline and neutral protease genes (Stahl and Ferrari, 1984; Yang et al., 1984; Kawamura and Doi, 1984).

Mutations within the coding sequence for flagellin itself may increase the efficiency by which some flagellin-protein "X" fusion proteins are exported. Presumably these mutations would be in sequences that encode for that portion of flagellin that is important for directing the transport of the fusion protein.

Should the co-presence in the same cell of the gene encoding the desired fusion protein and the host flagellin gene result in competition between the fusion protein and flagellin for the same export site machinery, the host flagellin may be inactivated to provide for more efficient export of flagellin fusion proteins. In the example described in the methods and results section, this was accomplished by integrating the expression vector, pIEV1fla304PIΔC, into the host flagellin gene. The integration event generated an active flagellin-proinsulin gene fusion, and simultaneously, inactivated the resident flagellin gene. The inactivation of the host flagellin gene can also be accomplished by replacing the gene with in vitro-derived deletion mutation (Stahl and Ferrari, 1984; Yang et al., 1984; Kawamura and Doi, 1984). This would increase the flexibility of using alternate vector-promoter combinations which may ultimately increase the yield of the desired product. The following are examples where the use of a host stain, from which all or part of the flgellin gene has been deleted, may be useful for increasing the product yield. The regulatory sequences for the initiation of transcription and translation of flagellin-gene "X" gene fusions in these examples may be those from the flagellin gene or may be from another gene where transcription and translation is constitutive; or these sequences may be from a gene that is regulated and thus could be controlled. The latter type of regulatory sequence may be used where it is desired to prevent gene expression until the culture density is high, at which point transcription and translation may then be initiated to yield product accumulation in the culture medium. Expression of genes encoding heterologous or homologous proteins controlled by any one of the above regulatory sequences may be on low-copy vectors such as integrable plasmids (Ferrari et al., 1983) or plasmids such as pE194 that replicate extrachromosomally (Gryczan and Dubnau, 1978) or high-copy vectors such as pUB110 (Gryczan et al., 1978) and pBE3 which replicate extrachromosomally. An integration vector may be inserted into any gene in the chromosome. A particularly attractive insertion site is a gene that is dispensable for normal growth, such as the neutral protease structural gene (Yang et al.,1984). This gene may be cloned and a portion of the coding sequence could be used as the homologous sequence on an integrable plasmid that is required for integration by recombination.

Genes or portins thereof for other portions of the flagellum, e.g. the hook or basal body proteins, may be used in place of the flagellin gene to achieve production and export of the heterologous protein. In such cases the protein may be recovered, purified and sequenced, in whole or part, and the gene encoding the protein identified by hybridization with oligonucleotide probes, for example, identification and use of such genes in accordance with this invention may be accomplished in analogous fashion to the methods disclosed herein for flagellin-related embodiments.

*E. coli* is certainly an attractive host for use in the flagellin export system. The flagellin gene can be easily cloned as described previously in this document and flagellin-heterologous gene fusions can be expressed as a part of low or high copy plasmid vectors or as sequences integrated into the chromosome. A mutation, cfs, has been isolated which when introduced into a strain results in a five-fold overproduction of flagellin and renders the strain constitutively motile (Silverman and Simon, 1977). Five-fold more flagellin-heterologous fusion protein may be produced if the appropriate vector containing the gene fusion is introduced into this mutant strain.

Literature Cited

Anagnostopoulos, C. and J. Spizizen. 1961. Requirements for transformation in *Bacillus subtilis*. J. Bacteriol. 81: 741-746.

Birnboim, H. C., and J. Doly. 1979. A rapid alkaline extraction procedure for screening recombinant plasmid DNA. Nucleic Acids Res. 7: 1513-1523.

Bolivar, F., R. L. Rodriguez, P. J. Greene, M. C. Betlachy, H. L. Heynecker, H. W. Boyer, J. H. Crosa, and S. Falkow. 1977. Construction and characterization of new cloning vehicles II. A multipurpose cloning system. Gene 2:95-113.

Burnette, W. N. 1981. "Western blotting": Electrophoretic transfer of proteins from sodium dodecyl sulfate-polyacrylamide gels to unmodified nitrocellulose and radiographic detection with antibody and radioiodinated protein A. Anal. Biochem. 112: 195-203.

Crea, R., and T. Horn. 1980. Synthesis of oligonucleotides on cellulose by a phosphotriester method. Nucleic Acids Res. 8: 2331-2348.

Dagert, M., and S. D. Ehrlich. 1979. Prolonged incubation in calcium chloride improves the competence of Escherichia coli cells. Gene 6: 23-28. Delange, R. J., J. Y. Change, J. H. Shaper, and A. M. Glazer. 1976. Amino acid sequence of flagellin of Bacilus subtilis 168. J. Biol. Chem. 254: 705-711.

Ferrri, F. A., A. Nguyen, D. Lang, and J. A. Hoch. 1983. Construction and properties of an integrable plasmid for Bacillus subtilis. J. Bacteriol. 154: 1513-1515.

Fraser, T. H., and B. J. Bruce. 1978. Chicken ovalbumin is synthesized and secreted by Escherichia coli. Proc. Natl. Acad. Sci. U.S.A. 75: 5836-5940.

Gill, P. R., and N. Agabian. 1982. A comparitive structural analysis of the flagellin monomers of Caulobacter crescentus indicated that these proteins are encoded by two genes. J. Bacteriol. 150: 925-933.

Gill, P. R., ajnd N. Agabian. 1983. The nucleotide sequence of the Mr=28,500 flagellin gene of Caulobacter crescentus. J. Biol. Chem. 258: 7395-7401.

Grant, G. F., and M. I. Simon. 1969.Synthesis of bacterial flagella II. PBS1 transduction of flagella-specific markers in B. subtilis. J. Bacteriol. 99: 116-124.

Grunstein, M., and D. Hogness. 1975. Colony hybridization: a method for the isolation of cloned DNAs that contain a specific gene. Proc. Natl. Acad. Sci. U.S.A. 72: 3961-3965.

Gryczan, T. J., S. Contente, and D. Dubnau. 1978. Characterization of Staphylococcus aureus plasmids introduced by transformation into Bacillus subtilis. J. Bacteriol. 134: 318-329.

Gutterson, N. I., and D. E. Koshland, Jr. 1983. Replacement and amplification of bacterial genes with sequences altered in vitro. Proc. Natl. Acad. Sci. U.S.A. 80: 4894-4898.

Hoch, J. A. 1976. Genetics of bacterial sporulation. Adv. Genet. 18: 69-98.

Hung, M-C., and P. C. Wensick. 1984. Different restriction enzyme-generated sticky DNA ends can be joined in vitro. Nucleic Acids. Res. 12: 1863-1874.

Iino, T. 1977. Genetics of structure and functions of bacterial flagella. Ann. Rev. Genet. 11: 161-182.

Joys, T. M., and V. Roukis. 1972. The primary structure of the phase-1 flagellar protein of Salmonella typhimurium. I. the tryptic peptides. J. Biol. Chem. 247: 5180-5193.

Kawamura, F., and R. H. Doi. 1984. Construction of a Bacillus subtilis double mutant deficient in extracellular alkaline and neutral proteases. J. Bacteriol. 160: 442-444.

Komeda, Y. 1982. Fusion of flagellar operons to lactose genes on a Mud lac bacteriophage. J. Bacteriol. 150: 16-26.

Laemmli, U. K. 1970. Cleavage of structural proteins during the assembly of the head of the bacteriophage T4. Nature 227: 680-685.

Lawn, R. M., J. Adelman, S. C. Bock, A. E. Franke, C. M. Houck, R. C. Najarian, P. H. Seeburg, and K. L. Wion. 1981. The sequence of human serum albumin cDNA and its expression in E. coli. Nucleic Acids. Res. 9: 6103-6114.

Maniatis, T., R. C. Hardison, E. Lucy, J. Laner, C. O'Connell, D. Quan, G. K. Sim, and A. Efstradiadis. 1978. The isolation of structural genes from libraries of eucaryotic DNA. Cell 15: 687-701.

Marmur, J. 1961. A procedure for the isolation of deoxyriubonucleic acid from microorganisms. J. Mol. Biol. 3: 208-218.

Maroux, S., J. Baratti, and P. Desnuelle. 1971. Purification and specificity of porcine enterokinase. J. Biol. Chem. 246: 5031-5039.

Marston, F. A. O., P. A. Lowe, M. T. Doel, J. M. Schoemaker, S. White, and S. Angal. 1984. Purification of calf prochymosin (prorennin) synthesized in Escherichia coli. Biotechnology 2: 800-804.

Martinez, R. J. 1963. A method for the purification of bacterial flagella by ion exchange chromatography. J. Gen. Microbiol. 33: 115-120.

Michel, J. F., and J. Millet. 1970. Physiological studies on early-blocked sporulation mutants of Bacillus subtilis. J. Appl. Bacteriol. 33: 220-227.

Millet, J. 1970. Characterization of proteinases excreted by Bacillus subtilis Marburg strain during sporulation. J. Appl. Bacteriol. 33: 207-219.

Nagai, K., and H. C. Thogersen. 1984. Generation of $\beta$-globin by sequence-specific proteolysis of a hybrid protein produced in Escherichia coli. Nature 309: 810-812.

Nilsson, B., e. Holmgren, S. Josephson, S. Gatenbeck, L. Philipson, and M. Uhlen. 1985. Efficient secretion and purification of human insulin-like growth factor I with a gene fusion vector in staphylococci. Nucleic Acids. Res. 13: 1151-1162.

Palva, I., P. Lehtovaara, L. Kaariainen, M. Sibakov, K. Cantell, C. H. Schein, K. Kashiwagi, and C. Weissman. 1983. Secretion of interferon by Bacillus subtilis. Gene 22: 229-235.

Perlman, D., and H. O. Halvorson. 1983. A putative signal peptidase recognition site and sequence in eucaryotic and procaryotic signal peptides. J. Mol. Biol. 167: 391-409.

Pooley, H. M., and D. Karamata. 1984. Genetic analysis of autolysin-deficient and flagellaless mutants of Bacillus subtilis. J. Bacteriol. 160: 1123-1129.

Randall, L. L. and S. J. S. Hardy. 1984. Export of protein in bacteria. Microbiol. Rev. 48: 290-298.

Richardson, C. C. 1971. Polynucleotide kinase from Escherichia coli infected with bacteriophage T4. Proc. Nucleic Acid Res. 2: 815-828.

Rigby, P. W. J., M. Dieckmann, C. Rhodes, and P. Berg. 1977. Labeling deoxyribonucleic acid to high specific activity in vitro by nick-translation with DNA polymerase I. J. Mol. Biol. 113: 237-251.

Sanger, F., S. Nicklen, and A. R. Coulson. 1977. DNA sequencing with chain-terminating inhibitors. Proc. Natl. Acad. Sci. U.S.A. 74: 5463-5467.

Scherer, S., and R. W. Davis. 1979.Replacement of chromosome segments with altered DNA sequences constructed in vitro. Proc. Natl. Acad. Sci. U.S.A. 76: 4951-4955.

Schoner, R. G., L. F. Ellis, and B. E. Schoner. 1985. Isolation and purification of protein granules from *Escherichia coli* cells overproducing bovine growth hormone. Biotechnology 3: 151–154.

Shortle, D., J. E. Haber, and D. Botstein. 1982. Lethal disruption of the yeast actin gene by integrative DNA transformation. Science. 217: 371–373.

Silhavy, T. J., S. A. Benson, and S. D. Emr. 1983. Mechanisms of protein localization. Microbiol. Rev. 47: 313–344.

Silverman, M., and M. Simon. 1977. Bacterial flagella. Ann. Rev. Microbiol. 31: 397–419.

Southern, E. M. 1975. Detection of specific sequences among DNA fragments separated by gel electrophoresis. J. Mol. Biol. 98: 503–517.

Spizizen, J. 1958. Transformation of biochemically deficient strains of *Bacillus subtilis* by deoxyribonucleate. Proc. Natl. Acad. Sci. U.S.A. 44: 1072–1078.

Stahl, M. L., and E. Ferrari. 1984. Replacement of the *Bacillus subtilis* subtilisin structural gene with an in vitro-derived deletion mutation. J. Bacteriol. 158: 411–418.

Suzuki, T., and Y. Komeda. 1981. Incomplete flagellar structures in *Escherichia coli* mutants. J. Bacteriol. 145: 1036–1041.

Talmadge, K., J. Brosius, and W. Gilbert. 1981. An 'internal' signal sequence directs secretion and processing of proinsulin in bacteria. Nature. 294: 176–178.

Vieira, J., and J. Messing. 1982. The pUC plasmids, and M13mp7-derived system for insertion mutagenesis and sequencing with synthetic universal primers. Gene. 19: 259–268.

Wahl, G. M., M. Stern, and G. R. Stark. 1979. Efficient transfer of large DNA fragments from agarose gels to diazobenzyloxymethyl-paper and rapid hybridization by using dextran sulfate. Proc. Natl. Acad. Sci. U.S.A. 76: 3683–3687.

Watson, M. F. F. 1984. Compilation of published signal sequences. Nucleic Acids. Res. 12: 5145–5164.

Wickner, W. 1979. The assembly of proteins into biological membranes: the membrane trigger hypothesis. Annu. Rev. Biochem. 48: 23–45.

Williams, D. C., R. M. VanFrank, W. L. Muth, and J. P. Burnett. 1982. Cytoplasmic inclusion bodies in *Escherichia coli* producing biosynthetic human insulin proteins. Science 215: 687–688.

Yang, M. Y., E. Ferrari, and D. J. Henner. 1984. Cloning of the neutral protease gene of *Bacillus subtilis* and the use of the cloned gene to create an in-vitro-derived deletion mutation. J. Bacteriol. 160: 15–21.

Yanisch-Perron, C., J. Vieira, and J. Messing. 1985. Improved M13 phage cloning vectors and host strains: nucleotide sequences of the M13mp18 and pUC19 vectors. Gene 33: 103–119.

Zeig, J., and M. Simon. 1980. Analysis of the nucleotide sequence of an invertable controlling element. Proc. Natl. Acad. Sci. U.S.A. 77: 4196–4200.

What is claimed is:

1. A method for producing a heterologous protein in a bacterial host cell such that the protein is exported from the host cell into the culture medium, the method comprising culturing in a bacterial culture medium a genetically engineered bacterial strain containing a fusion DNA sequence which comprises a first nucleotide sequence encoding at least an N-terminal portion of a flagellin protein native to the bacterial host cell species and a second nucleotide sequence encoding the heterologous protein, said first nucleotide sequence being linked via its 3' terminus to the 5' terminus of the second DNA sequence and said fusion DNA sequence being operatively linked to an expression control sequence and wherein said N-terminal portion results in the export of said heterologous protein.

2. A method according to claim 1 which further comprises recovering the exported protein from the culture medium.

3. A method according to claim 1, wherein the first and second nucleotide sequences of the fusion DNA sequence are linked by a linking nucleotide sequence which encodes a selectably cleavable polypeptide such that the exported protein contains a selectably cleavable site.

4. A method according to claim 3 which further comprises cleaving the exported protein at the selectably cleavable site to produce the heterologous protein encoded for by the second nucleotide sequence of the fusion DNA sequence.

5. A method according to claim 4 which further comprises recovering the heterologous protein from any polypeptide fragment of flagellin or other proteinaceous material.

6. A method according to claim 1, wherein the engineered bacterial cells are cultured in the presence of a substance which represses the production or export of proteases.

7. A method according to claim 1, wherein the fusion DNA sequence is integrated into the chromosome of the host cell.

8. A method according to claim 1, wherein the fusion DNA sequence is contained in an extrachromosomal plasmid within the host cell.

9. A method according to claim 2, wherein the exported protein is recovered by immunoaffinity chromatography using anti-flagellin antibody.

* * * * *